United States Patent [19]

Chu

[11] Patent Number: 4,565,446
[45] Date of Patent: Jan. 21, 1986

[54] SCATTERING CELLS

[75] Inventor: Benjamin Chu, Setauket, N.Y.

[73] Assignee: The Research Foundation of State University of New York, Albany, N.Y.

[21] Appl. No.: 427,115

[22] Filed: Sep. 29, 1982

[51] Int. Cl.[4] .............................................. G01N 1/10
[52] U.S. Cl. .................................... 356/246; 356/343
[58] Field of Search ................................. 356/338–343, 356/246, 440, 441, 128, 134, 135; 250/564, 574, 576; 73/61.1 C

[56] References Cited

U.S. PATENT DOCUMENTS

| | | | |
|---|---|---|---|
| 3,583,817 | 6/1971 | Rachlis et al. .................. | 356/246 X |
| 3,843,268 | 10/1974 | Kaye ................................... | 356/246 |
| 4,053,229 | 10/1977 | McCluney .......................... | 356/338 |

FOREIGN PATENT DOCUMENTS 1192849  5/1965  Fed. Rep. of Germany ...... 356/134

Primary Examiner—Davis L. Willis
Assistant Examiner—Matthew W. Koren
Attorney, Agent, or Firm—Omri M. Behr

[57] ABSTRACT

A scattering cell can contain a sample whose scattering properties upon irradiation are measurable by a detector. The cell includes a central body having an input and output side spanned by a sample cavity. The cell also has an input window bordering the sample cavity on the input side. Also included is a prismatic output window bordering the sample cavity on the output side. This output window is operable to refract its incident radiation and vary the angle between its incident and transmitted radiation as a function of its angle of incidence.

18 Claims, 7 Drawing Figures

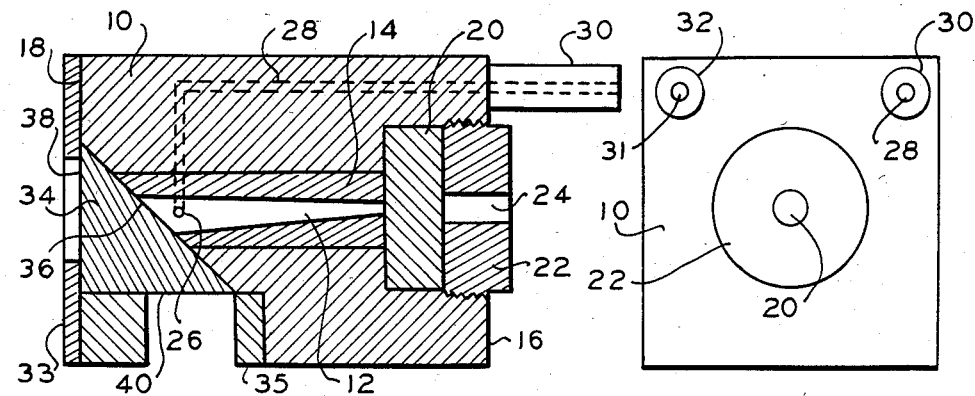
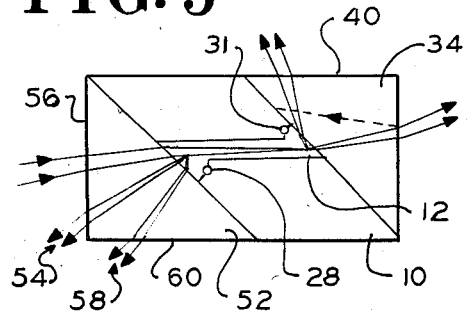
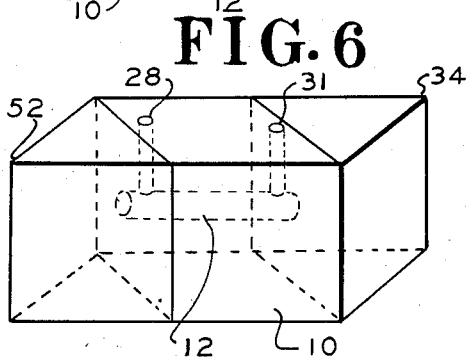
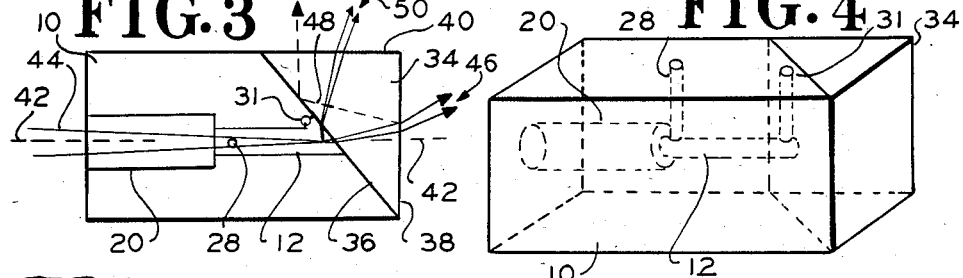
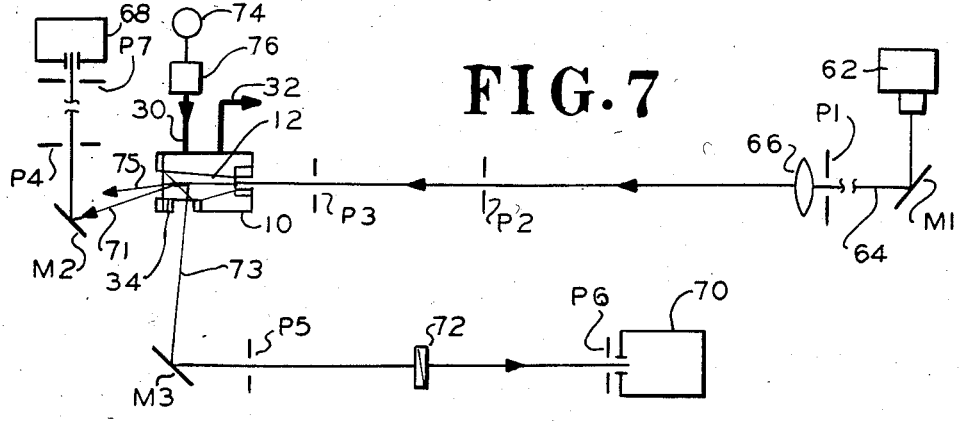

SCATTERING CELLS

BACKGROUND OF THE INVENTION

The present invention relates to scattering cells and, in particular, to cells designed to measure both relatively small scattering angles as well as large scattering angles.

Particles disposed in a medium having a different index of refraction than the particles can scatter light. In general, the intensity of the scattered light is a function of the wave length of the incident light, the size and concentration of the scattering particles, as well as the volume of the sample being irradiated. The scattering sample can transmit a direct and a scattered beam whose intensity ratio can be related to the Rayleigh factor to obtain an indication of molecular weight.

A well known method of analyzing the scattered intensity of light is by a Zimm plot. By extrapolating this plot to zero concentration at zero scattering angle, an estimate can be made of the reciprocal of molecular weight. In addition, various slopes of the Zimm plot relate to the redius of gyration of the scattering particles. In particular the second virial coefficient of the Zimm plot can be related to the non-ideality of the scattering particles, thereby characterizing the particles by their interaction with the medium and different surrounding particles. For certain scattering particles, the slopes of the Zimm plot may be linear out to very large scattering angles. Therefore it is desirable under these circumstances to obtain a plot extending from very small to very large angles.

In the past, equipment has been designed to measure very small scattering angles but has been unable to simultaneously obtain information regarding large scattering angles. It is advantageous to obtain such simultaneous measurements since the measurements are known to be definitely related to the same type of particles so that the validity of the data is confirmed.

Another class of useful data can be obtained from observing the frequency bandwidth or Doppler shifts caused by particle motion. This effect tends to broaden the line width of the spectrum transmitted from the scattering sample. By conventional spectrum analysis or by using autocorrelation techniques, these frequency effects can be evaluated to allow derivation of the diffusion coefficient of the particles. This coefficient bears a relation to the particles' size and shape and molecular weight. The diffusion coefficient measured in this fashion can vary as a function of the scattering angle. The manner in which this diffusion coefficient changes signifies the nature and number of the degrees of freedom of the particles. For very small scattering angles, the diffusion coefficient is related primarily to the translational degrees of freedom. Such information is very valuable for studying anisotropic particles. Other types of degrees of freedom may be revealed only at relatively large angles.

It is also known to analyze particles in a medium by subjecting them to size exclusion chromatography, for example, gel permeation chromatography and high pressure liquid chromatography. It is desirable to apply such methods contemporaneously with a light scattering test so the data is reliably correlated.

A practical problem with obtaining accurate scattering measurements is accounting for extraneous particles in the medium. The clarification required to exclude such extraneous particles can be time consuming and expensive. An advance has been achieved with the advent of highly focused lasers which concentrate coherent light within an extremely small volume. The probability therefore of an extraneous particle entering within this small volume becomes rather small and its presence is obvious. Another practical problem is designing a sample cell so that light passing within its windows does not reflect back into the scattering sample. Such reflections can cause an undesirable illumination of the sample resulting in a background noise that degrades the accuracy of the measurement, expecially at very low angles.

One known technique (U.S. Pat. No. 3,843,268) for overcoming the internal reflections within the window of a sample cell involves using relatively thick windows. These thick windows provide a relatively long optical path so that light internally reflected by the window has less of a tendency to return to the sample volume. Unfortunately the design of the exit windows in U.S. Pat. No. 3,843,268 permits 180° back reflections at the air/glass interface allowing incident light to reenter the scattering volume. Thus the scattering volume has incident beams in opposite direction with the reflected beam having an intensity of about 4% of the main beam. Another disadvantage with this type of system is that its use of relatively thick windows prevents measurements at relatively high scattering angles. Also the system does not attempt to increase the angular resolution for measurements at very low scattering angles.

Accordingly, there is a need for a scattering cell which is able to measure contemporaneously light scattered at relatively low and relatively large scattering angles and to perform these measurements with improved resolution.

SUMMARY OF THE INVENTION

In accordance with the illustrative embodiments demonstrating features and advantages of the present invention, there is provided a scattering cell for containing a sample whose scattering properties upon irradiation can be measured by a detector. The cell includes a central body, an input window and a prismatic output window. The central body has an input and output side spanned by a sample cavity. The input window borders the sample cavity on the input side and the prismatic output window borders the sample cavity on the output side. This output window is operable to refract its incident radiation and vary the angle between its incident and transmitted radiation as a function of its angle of incidence.

Such a cell can be used with a source of radiation aimed at the input window. A detection means can contemporaneously detect radiation transmitted from the prismatic output window through two different angular ranges.

A method according to the same invention can measure the scattering properties of a sample with a sample cell of the foregoing type. The method includes the steps of disposing the sample in the cell against the output window and directing radiation through the sample toward the output window. The method also includes the step of detecting radiation scattered through the sample and refracted by the prismatic output window.

By employing the foregoing apparatus and method, an improved measurement system is obtained. In the preferred embodiment, the output window of the scattering cell is in the shape of a prism having a triangular cross-section. The light incident to the prism is refracted thereby. As a result, the angular separation between the unscattered and scattered light is increased. This results in an improved resolution enabling an operator to obtain reliable information at relatively low scattering angles near the normally intense direct, unscattered beam. Furthermore, the preferred prismatic window has a lateral face positioned to allow transmission and detection at relatively large scattering angles. Additionally, the optics of the prism are such that light reflected internally within the prism does not tend to return to the scattering volume. This latter feature effectively reduces the background noise and interference caused by unintended illumination of the sample.

In a preferred embodiment a single, highly focused laser beam is directed through the sample volume which is surrounded by a black conical liner. Detectors are posted at the two output faces of the prism to simultaneously measure low and high scattering angles.

The preferred scattering cell has a body which contains inlet and outlet ducts communicating with the sample cavity at its lowermost and uppermost points. The latter configuration improves fluid flow and tends to remove bubbles from the light path.

BRIEF DESCRIPTION OF THE DRAWINGS

The above brief description as well as other objects, features and advantages of the present invention will be more fully appreciated by reference to the following detailed description of the presently preferred but nontheless illustrative embodiments in accordance with the present invention when taken in conjunction with the accompanying drawings wherein;

FIG. 1 is a top cross-sectional view of a sample cell according to the principles of the present invention;

FIG. 2 is an end view of the input side of the cell of FIG. 1;

FIG. 3 is a schematic diagram of the cell of FIG. 1, showing its light paths;

FIG. 4 is a schematic perspective view of the cell of FIG. 3;

FIG. 5 is a top schematic view of an alternate sampling cell similar to that of FIG. 1 but including a prismatic input window;

FIG. 6 is a schematic perspective view of the cell of FIG. 5; and

FIG. 7 is a schematic illustration of a system employing the scattering cell of FIG. 1.

DETAILED DESCRIPTION OF THE PREFERRED EMBODIMENTS

Referring to FIGS. 1 and 2, a scattering cell is illustrated employing a central body 10 in the form of a rectangular block having a sample cavity 12 containing a sample such as a polymer, colloid or other substance disposed in an appropriate medium. In this embodiment the sample cavity is lined with a black plastic liner 14 made of a Teflon plastic although other non-reactive materials can be used instead. The outside of liner 14 matches the bore in body 10, both being cylindrical. The internal bore of liner 14 is frustroconical and flares in a direction from input side 16 to output side 18 of body 10. Mounted in a cylindrical counter bore on input side 16 of central body 10, is cylindrical input window 20. Input window 20 is held in place by annular cap 22 having external threads matching internal threads in central body 10. Concentric bore 24 in cap 22 is aligned with sample cavity 12.

Near the frustroconical base of cavity 12 is a transverse aperture 26, vertically piercing the side of liner 14. Positioned in this fashion, aperture 26 is at the lowest point in cavity 12. A conduit 28 is drilled through body 10 to allow aperture 26 to communicate with inlet 30. An identical aperture (schematically illustrated hereinafter) is located vertically above aperture 26 in liner 14 at the high point of cavity 12. Conduit 31 bored through body 10 allows communication with the high point of liner 14 to outlet 32. The upper portion of cavity 12 communicating with outlet 32 is referred to herein as an upper concavity while the lower portion of sample cavity 12 communicating with inlet aperture 26 is referred to herein as a lower concavity.

One corner of rectangular body 10 at output side 18 is truncated along a vertical plane. At this truncation, contiguous to output side 18 and to sample cavity 12 is prismatic output window 34, shown herein in the shape of a prism having a triangular cross-section. While prism 34 is shown herein as a 45° right triangle, various other angles can be employed instead. In a preferred embodiment prism 34 is a conventional prism having highly polished surfaces. The three functional surfaces of prism 34 are referred to herein as inner face 36, outer face 38, and lateral face 40, the lateral and outer face being orthogonal to each other and disposed at 45° to inner face 36. Secured against faces 38 and 40 are rectangular cover plates 33 and 35, respectively, each having rectangular apertures.

Referring to FIGS. 3 and 4, an essentially schematic diagram is given of the apparatus of FIGS. 1 and 2. However a modification is suggested in that conduits 28 and 31 are shown emerging vertically upward from the input and output end, respectively, of sample cavity 12. The sampling cell is shown partitioned by vertical plane 42 which contains the centerline of the incoming radiation: converging laser light beam 44. Beam 44 is illustrated with an exaggerated angle of convergence, focusing at inner face 36 of prism 34. Unscattered light and light scattered through a relatively small angle is illustrated as beam 46. It will be noted that beam 46 has refracted across inner face 36 so it deflects to the left (that is, to a given side of plane 42) since in this case, the index of refraction of the prism exceeds that of the sample. Similarly, beam 46 is further refracted to the left at outer face 38. It is significant to note that beam 46 intercepts outer face 38 at a non-orthogonal angle. Accordingly, internal reflections do not tend to return to scattering volume 12. Instead such internally reflected light is shown returning along reflection path 48. If this reflected light is not trapped it can be used as it emerges from face 40 as a local oscillator for heterodyning the neighboring scattered light.

Also, relatively large angles of scattering can occur in cavity 12 in the vicinity of inner prism surface 36. Such large angles of scattering can result in beam 50. Beam 50 will be refracted at surface 36 to deflect to the left (away from plane 42). Upon reaching lateral face 40, with the angles illustrated (that is, the internal beam still slanting toward outer face 38), beam 50 will refract to the right. Significantly, the prism 34 as configured can readily transmit beams scattered at large angles and allow their detection through lateral face 40.

Referring to FIGS. 5 and 6, an embodiment which is an alternate to that of FIGS. 1–4 is illustrated. In these figures, elements bearing the same reference numerals as previously employed, are components having the same function and similar structure. An important difference in the embodiment of FIGS. 5 and 6 is the replacement of the previously illustrated input window with prismatic input window 52. In this embodiment window 52 is a prism identical to previously described prismatic output window 34. By using this type of input window, relatively large scattering angles between 90° to 180° that are not easily transmitted through face 40 can be analyzed. In particular, one such highly scattered beam 54 is shown being transmitted through rear face 56 of prism 52. Another less highly scattered beam 58 is shown being transmitted through lateral face 60 of input prismatic window 52. It again will be appreciated that the various angles of convergence and divergence may have been exaggerated to clarify the illustration.

Referring to FIG. 7, the scattering system illustrated herein employs source of radiation 62 producing, in this preferred embodiment, monochromatic coherent laser light. While visible radiation is preferred, other frequencies may be employed in different embodiments. Output beam 64 from laser 62 is perpendicularly reflected by mirror M1 through pinhole aperture P1 through collimating and focusing lens 66. Lens 66 projects beam 64 through pinhole apertures P2 and P3 before illuminating scattering cell 10. Light emerging from cell 10 can be detected by a detection means shown herein as first detector 68 and second detector 70. One light beam incident on prism 34 and refracted thereby is shown emerging from its outer face as beam 71 to be reflected to the right by rotatable mirror M2 and transmitted through pin apertures P4 and P7 to detector 68. Unscattered light beam 75 will, if reflected by mirror M2, be blocked by pin aperture P4. Accordingly, the scattering angles of light accepted by photomultiplier 68 can be conveniently selected by rotating mirror M2.

Another light beam incident on prism 34 and refracted thereby is shown emerging from its lateral face as beam 73 which is reflected to the left by rotatable mirror M3. Laser light reflected by mirror M3 is transmitted through pinhole aperture P5 and through analyzer 72 which, in this embodiment, is essentially a polarizing filter. Light transmitted through polarizing filter 72 passes through a final pinhole aperture P6 before reaching detector 70. Again the scattering angle of light accepted by detector 70 can be adjusted by rotating mirror M3. Each of the detectors 68 and 70 can contain a photomultiplier tube providing data to a system for analyzing the intensity and spectrum of the incoming laser light. In particular, the line-width of the incoming spectrum can be studied. In one preferred embodiment detectors 68 and 70 employ a multi-channel autocorrelator for performing the well-known autocorrelation function on discrete time samples to characterise the line-width of incoming light.

Mirror M1 is spaced 60 millimeters from laser 62 and 125 millimeters from aperture P1. Lens 66 is separated by 90 millimeters from aperture P1 and by 265 millimeters from aperture P2. Aperture P3 is spaced 55 millimeters from cell 10 and 140 millimeters from aperture P2. The spacing between cell 10 and mirrors M3 and M2 is 125 and 70 millimeters, respectively, while the spacing between apertures P5 and P6 is 300 millimeters. The spacing between aperture P4 and detector 68 is 420 millimeters. It will be appreciated that the foregoing dimensions can be readily altered depending upon the application.

Sample cavity 12 can be supplied with a sample from sample source 74 through serially connected apparatus 76. Apparatus 76 performs size exclusion chromatography, for example, gel permeation chromatography or high pressure liquid chromatography. The output of apparatus 76 is fed through line 30 to sample cavity 12 which is drained by outlet 32.

To facilitate an understanding of the principles associated with the apparatus of FIGS. 1–4 and 7, its operation will be briefly described. It will be appreciated that the operation of the apparatus of FIGS. 5 and 6 are similar except that its prismatic input window allows analysis of scattered light over a larger angular range.

Source 74 (FIG. 7) may provide a sample stream of colloids, polymers, or other substances disposed in an appropriate medium. Source 74 feeds chromatographic or filtration apparatus 76. Accordingly, the particles initially arriving in inlet 30 and entering cavity 12 can be larger particles which may or may not be of most interest to the experimenter. Collimated laser light beam 64 enters cell 10 and illuminates the sample in cavity 12. Since beam 64 is narrowly focused, the scattering volume illuminated is extremely small and the likelihood of extraneous particles entering the illuminated scattering volume to cause erroneous readings is rather small.

Unscattered light is refracted through prism 34, emerging as beam 75 which if reflected by mirror M2 does not pass through pinhole aperture P4 and is therefore effectively blocked from detection. However, light scattered at a relatively small angle can emerge from the outer face of prism 34 along beam path 71. It will be observed that prism 34 operates to increase the angle separating beams 75 and 71. This phenomena is due to the tendency of the prism to increase divergence among certain rays. Beam 71 is ultimately projected into the photomultiplier tube of detector 68 to stimulate its multichannel autocorrelation system. In addition, strongly scattered light emerges from the lateral face of prism 34 along beam 73. This light is also refracted by prism 34 and account must be taken of the apparent change in angle resulting from the prismatic refraction. Beam 73 is analysed by polarizer 72 which admits only light polarized in one specific orientation into detector 70. The experimenter can obtain the angular distribution of data by adjusting mirrors M2 and M3 to select the desired scattering angle.

It will be appreciated that since the divergence between direct beam 75 and scattered beam 71 has been increased, relatively small scattering angles can be measured without interference. Therefore the associated Zimm plots can be extended to extremely small angles. This feature is useful in obtaining an accurate indication of molecular weight as previously mentioned. Additionally, the diffusion coefficient can be obtained at extremely small angles which allows analysis of translational degrees of freedom, these degrees being evidenced primarily by spectral data in light scattered at small angles. This latter feature is especially significant when studying polydispersed systems.

Additionally, relatively large scattering angles can be detected by detector 70. These large scattering angles are significant when Zimm plots are being obtained for substances having sizes comparable to the wavelength of the incident radiation. Of course, these large scattering angles can be significant where spectral data must be studied at large scattering angles to characterize certain degrees of freedom of the scattering particle evidenced only at these large angles. It is also advantageous to obtain measurements at small and large scattering angles simultaneously. Simultaneous measurements ensures that the data relates to the same type of particles and that the data is validly correlated.

As the chromatographic apparatus 76 continues to supply smaller particles, the data can then be reanalyzed to characterize the new class of particles entering sample chamber 12. It is highly advantageous to be able to obtain large and small scattering angle data in one experiment, sequentially obtaining data for different size particles.

Also the refractive index of the sample in cavity 12 can be obtained by observing the extent of refraction caused by prism 34. The refractive index of prism 34 is presumably known.

It is to be appreciated that various modifications may be implemented with respect to the above described preferred embodiment. For example, the size and shape of the prism, including the angles between the various faces can be altered depending upon the application. In addition, the shape of the main body and the liner for the sample cell can be changed depending upon the desired volume, flow rate and flow characteristics. Furthermore, while a conical cavity is illustrated it will be appreciated that spherical or other shapes may be employed. It is, however, desirable to have a lower and upper concavity for allowing filling and draining, the upper concavity being advantageously used as a bubble trap. Also, while glass prisms are preferred other optical substances having different optical qualities can be employed instead. Furthermore the dimensions of and materials in various components can be altered depending upon the desired sample volume, speed of analysis, sample temperature etc.

Obviously many modifications and variations of the present invention are possible in light of the above teachings. It is therefore to be understood that within the scope of the appended claims, the invention may be practiced otherwise than as specifically described.

What is claimed is:

1. A scattering cell for containing a sample whose scattering properties upon irradiation are measured by a detector, comprising:

a central body having an input and output side spanned by a sample cavity along a cavity axis, said output side ending in an output opening:

a input window bordering said sample cavity on said input side; and a prismatic output window bordering said sample cavity on said output side, said output window being operable to refract its incident radiation and vary the angle between its incident and transmitted radiation as a function of its angle of incidence, said prismatic window having a refractive index relative to said sample for causing a given deflection between said incident and transmitted radiation for unscattered axial rays of said incident radiation parallel to said cavity axis, said output opening and said prismatic output window being sized with respect to said given deflection to prevent said unscattered axial rays from being internally reflected within said prismatic output window back into said output opening.

2. A scattering cell according to claim 1 wherein said prismatic output window has contiguous to said body an inner face and an outer face disposed at an acute angle to said inner face.

3. A scattering cell according to claim 2 wherein said prismatic output window has the shape of a prism with a triangular, transverse cross-section.

4. A scattering cell according to claim 2 wherein said body has an inlet and outlet communicating with said cavity at spaced positions therein.

5. A scattering cell according to claim 4 wherein said cavity has an upper and lower concavity, said inlet and outlet communicating with said lower and upper concavity, respectively.

6. A scattering cell according to claim 5 wherein said cavity is a frustroconical cavity, said upper and lower concavities being located at opposite sides of the base of said frustoconical cavity, the interior surface of said cavity being substantially non-reflective.

7. A scattering cell according to claim 2 wherein said prismatic output window has a lateral face disposed at an angle to said inner and outer face, said prismatic output window being positioned with respect to said detector to transmit scattered radiation from said cavity through said lateral face to said detector.

8. A scattering cell according to claim 7 wherein said input window is thick, the thickness of said input window being sized to reduce light internally reflected within said input window and reaching said cavity, below a predetermined magnitude.

9. A scattering cell according to claim 7 wherein said input window has the shape of a prism with a triangular, transverse cross-section.

10. A scattering system for irradiating a sample and measuring its scattering properties comprising:

(a) a scattering cell including a central body having an input and output side spanned by a sample cavity along a cavity axis, said output side ending in an output opening, said cell having an input window and a prismatic output window bordering said cavity on the input and output side, respectively, said output window being operable to refract its incident radiation and vary the angle between its incident and transmitted radiation as a function of its angle of incidence, said prismatic window having a refractive index relative to said sample for causing a given deflection between said incident and transmitted radiation for unscattered axial rays of said incident radiation parallel to said cavity axis, said output opening and said prismatic output window being sized with respect to said given deflection to prevent said unscattered axial rays from being internally reflected within said prismatic output window back into said output opening;

(b) a source of radiation aimed at said input window; and (c) detection means for contemporaneously detecting radiation transmitted from said prismatic output window at two different angles at least.

11. A scattering system according to claim 10 wherein said detection means comprises a pair of spaced radiation detectors.

12. A scattering system according to claim 10 or 11 wherein said prismatic output window is operable to refract radiation more strongly from a path near a predetermined plane to a given side thereof, said detection means being operable to detect radiation refracted to said given side of said predetermined plane by said prismatic window.

13. A method for measuring the scattering properties of a sample with a sample cell having a prismatic output window for refracting radiation and varying the angle between incident and transmitted radiation of the window as a function of the angle of incidence, said prismatic window being operable to refract incident radiation more strongly from a path near a predetermined plane to a given side thereof, comprising the steps of:

disposing said sample in said cell against said window;

directing radiation through said sample toward said output window;

detecting radiation scattered through said sample and refracted by said prismatic output window in a predetermined solid angle of transmitted radiation refracted to said given side of said predetermined plane; and urging said sample to flow past said window.

14. A method for measuring the scattering properties of a sample with a sample cell having a prismatic output window for refracting radiation and varying the angle between incident and transmitted radiation of the window as a function of the angle of incidence, comprising the steps of:

disposing said sample in said cell against said window;

directing radiation through said sample toward said output window;

detecting radiation scattered through said sample and refracted by said prismatic output window;

urging said sample to flow past said window; and discriminating by particle size to allow larger and smaller particles in said sample to flow past said window at different times, on the average.

15. A method according to claim 14 wherein said window has an inner face contiguous to said sample, an outer face disposed at an acute angle to said inner face and a lateral face disposed at an angle to said inner and outer face, wherein the step of detecting radiation includes:

detecting a predetermined solid angle of refracted radiation transmitted through said outer face; and contemporaneously detecting a given solid angle of refracted radiation transmitted through said lateral face.

16. A method for measuring the scattering properties of a sample with a sample cell having a prismatic output window for refracting radiation and varying the angle between incident and transmitted radiation of the window as a function of the angle of incidence, comprising the steps of:

disposing said sample in said cell against said window;

directing radiation through said sample toward said output window;

detecting radiation scattered through said sample and refracted by said primatic output window;

urging said sample to flow past said window; and measuring the amount of refraction caused by the interface of said sample and window to obtain the index of refraction of said sample with respect to said window.

17. A scattering cell for containing a sample whose scattering properties upon irradiation are measured by a detector, comprising:

a central body having an input and output side spanned by a sample cavity, said body having an inlet and outlet communicating with said cavity at spaced positions therein, said cavity having an upper and lower concavity, said inlet and outlet communicating with said lower and upper concavity, respectively;

an input window bordering said sample cavity on said input side; and a prismatic output window bordering said sample cavity on said output side, said output window being operable to refract its incident radiation and vary the angle between its incident and transmitted radiation as a function of its angle of incidence, said prismatic output window having contiguous to said body an inner face and an outer face disposed at an acute angle to said inner face.

18. A method for measuring the scattering properties of a sample with a sample cell having a prismatic output window for refracting radiation and varying the angle between incident and transmitted radiation of the window as a function of the angle of incidence, said window having an inner face contiguous to said sample, an outer face disposed at an acute angle to said inner face and a lateral face disposed at an angle to said inner and outer face, comprising the steps of:

disposing said sample in said cell against said window;

directing radiation through said sample toward said output window;

detecting radiation scattered through said sample and refracted by said prismatic output window by: (a) detecting a predetermined solid angle of refracted radiation transmitted through said outer face; and (b) contemporaneously detecting a given solid angle of refracted radiation transmitted through said lateral face; and urging said sample to flow past said window.

* * * * *